US012790393B2

(12) United States Patent
Jeon et al.

(10) Patent No.: US 12,790,393 B2
(45) Date of Patent: Nov. 10, 2026

(54) ANTI-CNTN4-SPECIFIC ANTIBODIES AND USE THEREOF

(71) Applicant: GENOME AND COMPANY, Seongnam-si (KR)

(72) Inventors: Bu Nam Jeon, Seongnam-si (KR); Youn Kyung Houh, Seongnam-si (KR); Yun Yeon Kim, Seongnam-si (KR); Mi Young Cha, Seongnam-si (KR)

(73) Assignee: GENOME AND COMPANY, Seongnam-si (KR)

( * ) Notice: Subject to any disclaimer, the term of this patent is extended or adjusted under 35 U.S.C. 154(b) by 473 days.

(21) Appl. No.: 18/288,268

(22) PCT Filed: Apr. 29, 2021

(86) PCT No.: PCT/KR2021/005449
§ 371 (c)(1),
(2) Date: Oct. 25, 2023

(87) PCT Pub. No.: WO2022/231032
PCT Pub. Date: Nov. 3, 2022

(65) Prior Publication Data
US 2024/0209081 A1 Jun. 27, 2024

(51) Int. Cl.

| | |
|---|---|
| ***C07K 16/28*** | (2006.01) |
| ***A61K 39/00*** | (2006.01) |
| ***A61P 35/00*** | (2006.01) |
| ***C12N 15/63*** | (2006.01) |
| ***G01N 33/575*** | (2026.01) |
| ***G01N 33/68*** | (2006.01) |

(52) U.S. Cl.
CPC .......... *C07K 16/2803* (2013.01); *A61K 39/00* (2013.01); *A61P 35/00* (2018.01); *C07K 16/2818* (2013.01); *C12N 15/63* (2013.01); *G01N 33/575* (2026.01); *G01N 33/68* (2013.01); *A61K 2039/505* (2013.01); *C07K 2317/70* (2013.01); *C07K 2317/92* (2013.01)

(58) Field of Classification Search
CPC ...... A61P 35/00; G01N 33/575; G01N 33/68; A61K 39/00; A61K 2039/505; C07K 16/2818; C07K 16/2803; C07K 2317/70; C07K 2317/92; C12N 15/63
See application file for complete search history.

(56) References Cited

U.S. PATENT DOCUMENTS

| | | | |
|---|---|---|---|
| 2019/0310261 A1 | 10/2019 | Park et al. | |
| 2020/0263258 A1 | 8/2020 | Boardman et al. | |

FOREIGN PATENT DOCUMENTS

| | | | |
|---|---|---|---|
| KR | 10-2019-0116930 A | 10/2019 | |
| WO | WO-2008051326 A2 * | 5/2008 | ......... C07K 14/4711 |
| WO | 2019/194586 A1 | 10/2019 | |
| WO | 2022/216014 A1 | 10/2022 | |

OTHER PUBLICATIONS

Anonymous, "CAS:2021_1832988_2862866097_1", XP093244396, Aug. 23, 2021, pp. 1 (1 page total).
Anonymous, "GSP:BJX22659", XP093244397, Aug. 23, 2021, pp. 1 (1 page total).
Extended European Search Report dated Feb. 24, 2025 from the European Patent Office in Application No. 21939415.2.
Anonymous, "immunoglobulin heavy chain variable region, partial [*Homo sapiens*]", Protein—NCBI,, Jul. 26, 2016, pp. 2, GenBank: AAM75838.1.
Anonymous, "immunoglobulin light chain variable region, partial [*Homo sapiens*]", Protein—NCBI, Aug. 5, 2020, pp. 1, GenBank: QMI58189.1.
Lucie Evenepoel et al., "Expression of Contactin 4 Is Associated With Malignant Behavior in Pheochromocytomas and Paragangliomas", The Journal of Clinical Endocrinology & Metabolism, Jan. 2018, pp. 46-55, vol. 103, No. 1.
International Search Report for PCT/KR2021/005449 dated Jan. 24, 2022.

* cited by examiner

*Primary Examiner* — Peter Johansen
(74) *Attorney, Agent, or Firm* — Sughrue Mion, PLLC

(57) ABSTRACT

The present invention relates to anti-CNTN4 antibodies or antigen-binding fragments thereof, and use thereof for activating T cells that upregulate a cell-mediated immune response, for example, use thereof for the treatment of cancer.

19 Claims, 8 Drawing Sheets

Specification includes a Sequence Listing.

[Fig. 1]
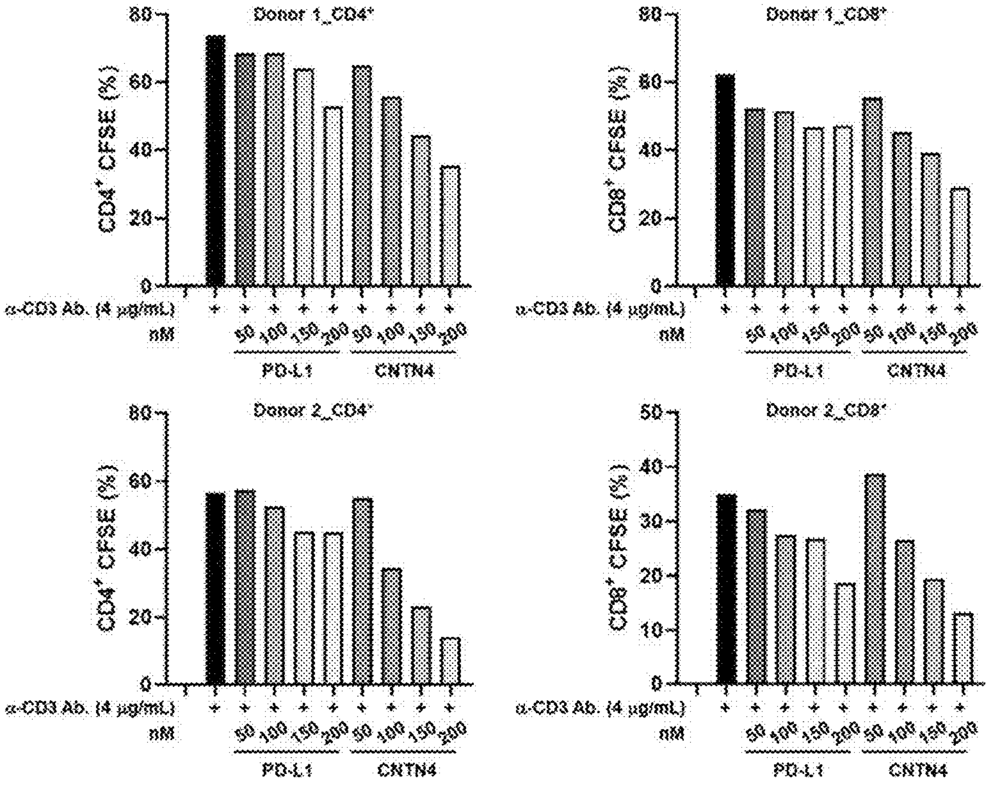
[Fig. 2]
| | |
|---|---|
| hAb-1 light chain variable region(VL) | ELTQDPAVSVALGQTVRITCSGSSGSYGWYQQKPGQAPVLVIYDNTNRPSGIPDRFS GSSSGNTASLTITGAQAEDEADYYCGGYDGSTDVFGGGTKLTVL |
| hAb-1 heavy chain variable region(VH) | EVQLLESGGGLVQPGGSLRLSCAASGFTFSSFNMFWVRQAPGKGLEWVAEISGGG GSTWYAPAVKGRFTISRDNSKNTLYLQMNSLRAEDTAVYYCAKSADTWSYGAATIDA WGQGTLVTVSS |

[Fig. 3]
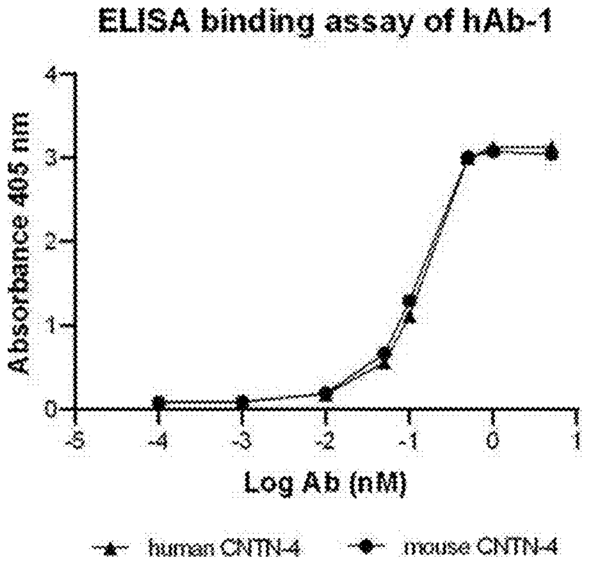
[Fig. 4]
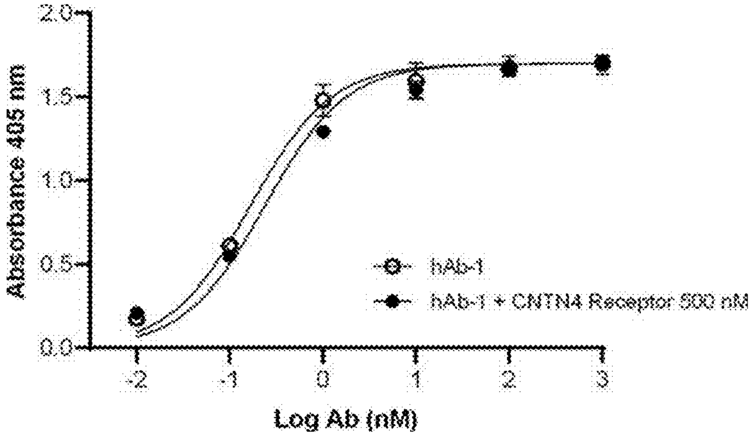

[Fig. 5]
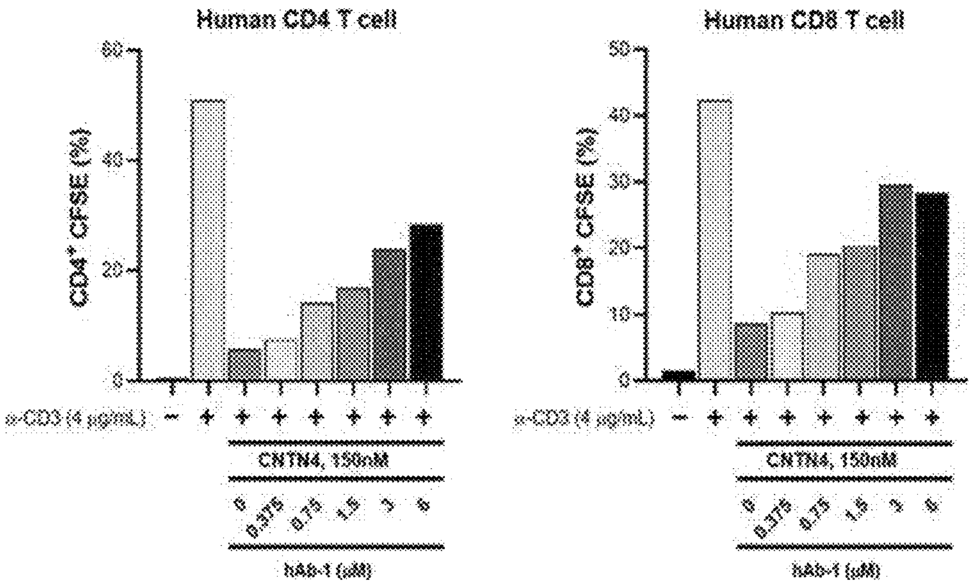
[Fig. 6]
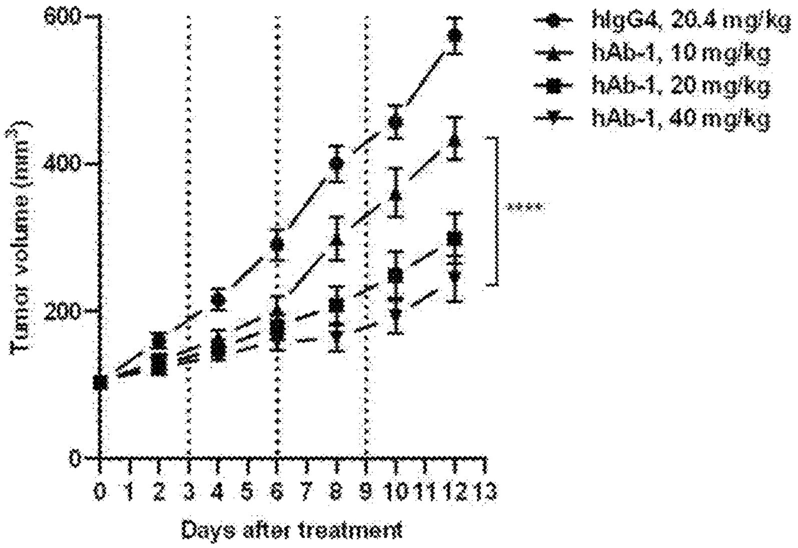

[Fig. 7]
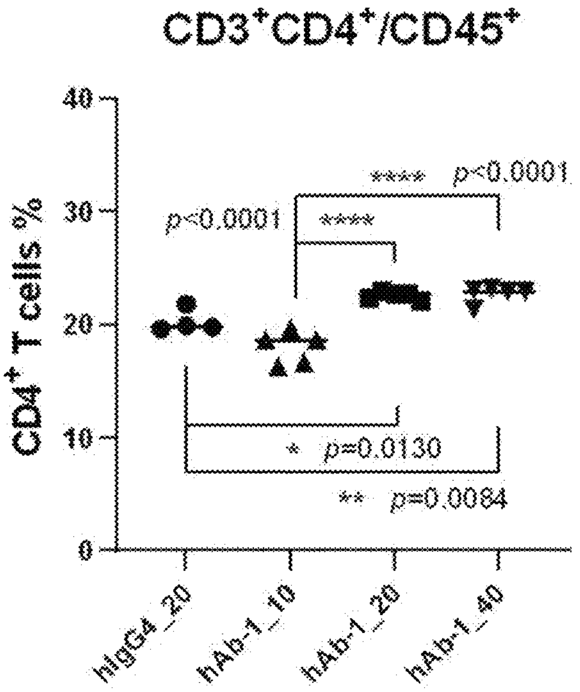
[Fig. 8]
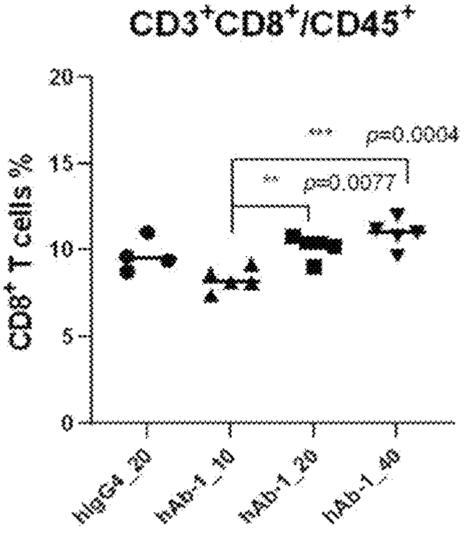

[Fig. 9]
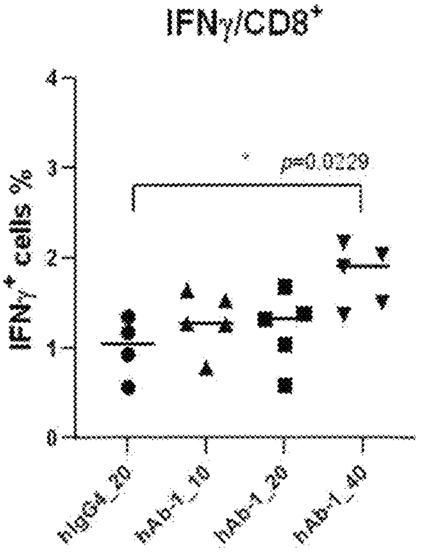
[Fig. 10]
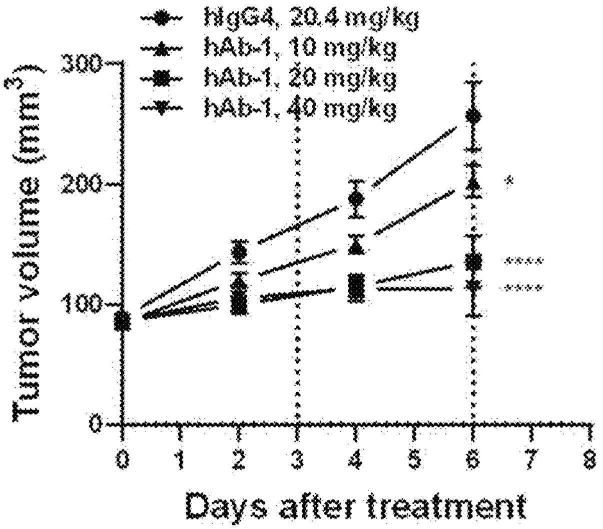

[Fig. 11]
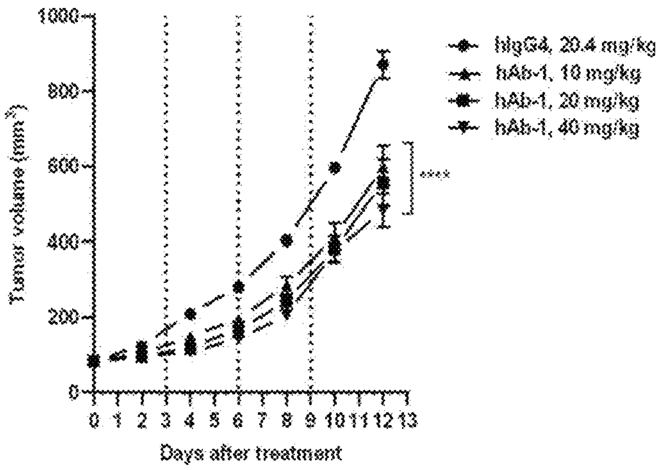
[Fig. 12]
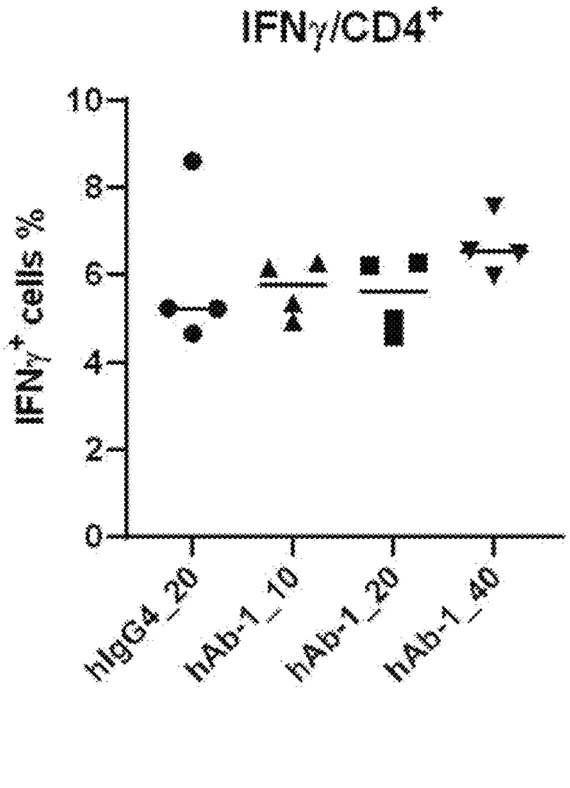

[Fig. 13]
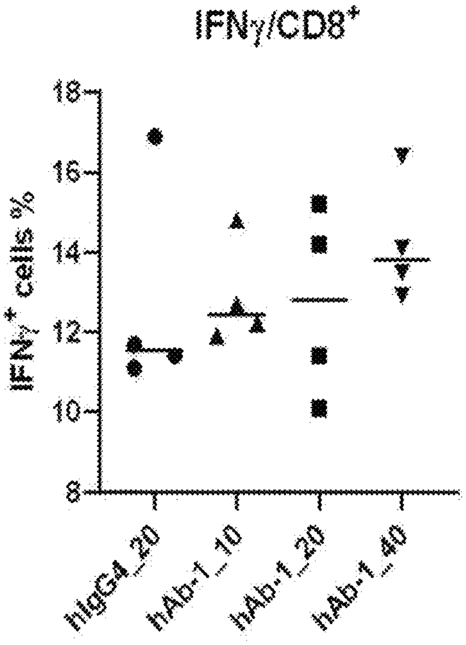
[Fig. 14]
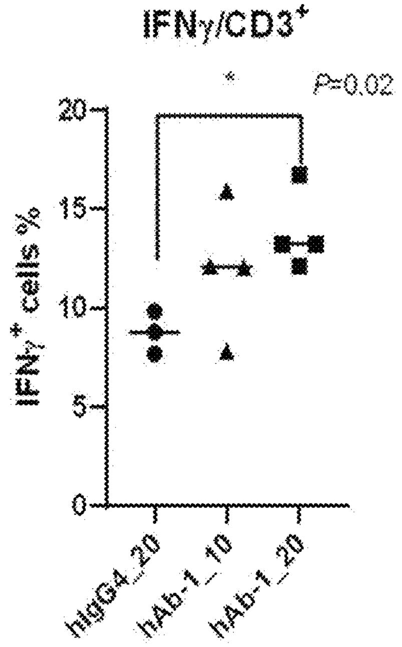

[Fig. 15]
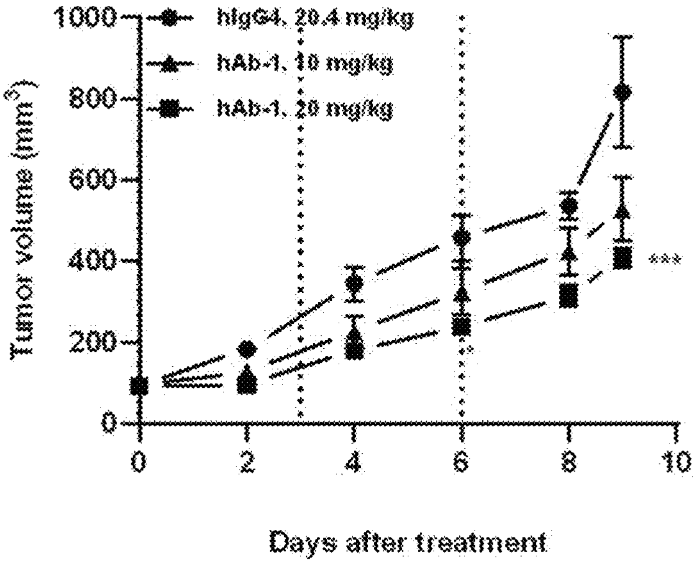

ANTI-CNTN4-SPECIFIC ANTIBODIES AND USE THEREOF

CROSS REFERENCE TO RELATED APPLICATIONS

This application is a National Stage of International Application No. PCT/KR2021/005449 filed Apr. 29, 2021.

INCORPORATION BY REFERENCE OF SEQUENCE LISTING

The content of the electronically submitted sequence listing, file name: Q292461_sequence listing as filed.XML; size: 2,421 bytes; and date of creation: Oct. 11, 2023, filed herewith, is incorporated herein by reference in its entirety.

TECHNICAL FIELD

The present invention relates to an anti-CNTN4 specific antibody or an antigen-binding fragment thereof, a therapeutic composition containing the same, and a use thereof for activating T cells, for example, for treating cancer.

BACKGROUND ART

The human body has a defense system that protects itself from external invaders (viruses, toxins, or the like) and internal harmful changes (cancer cell mutations). Unlike normal cells, cancer cells have specific antigens on the surface thereof and are destroyed by the immune system at an early stage of cancer development. Then, when the balance of the power of cancer cells, which want to proliferate indefinitely, and immune cells, which want to attack the cancer cells, collapses, the cancer cells begin to proliferate substantially. When cancer cells grow further, they disturb the immune system in the body, and some cancer cells avoid immunity by using the immune checkpoint of immune cells, and when immune checkpoint inhibitors suppress the immune checkpoint, the power of immune cells increases, thereby killing the cancer cells.

Immune checkpoint inhibitors are drugs that attack cancer cells by activating T cells by blocking the activation of immune checkpoint proteins involved in T cell inhibition, and include CTLA-4, PD-1, PD-L1 inhibitors, or the like. Representative drugs, which are currently commercially available, include ipilimumab (product name: YERVOY®) as CTLA-4 monoclonal antibodies, nivolumab (product name: OPDIVO®) and pembrolizumab (product name: KEYTRUDA®) as PD-1 monoclonal antibodies, and atezolizumab (product name: TECENTRIQ®) and durvalumab (product name: IMFINZI®) as PD-L1 monoclonal antibodies.

However, there are still carcinomas that are not treated with existing immune checkpoint inhibitors, and thus the development of new anticancer treatments is required.

Korean Patent Application Laid-open Publication No. 10-2019-0116930 discloses that CNTN4 can be used as a new target for cancer treatments using the human immune system. The above Korean patent application discloses that CNTN4 inhibits T cell activity.

PRIOR ART DOCUMENT

Patent Document

Korean Patent Application Laid-open Publication No. 10-2019-0116930

DISCLOSURE OF THE INVENTION

Technical Problem

The purpose of the present invention is to provide an anti-CNTN4 antibody or an antigen-binding fragment thereof, which specifically binds to a CNTN4 protein. In particular, the present invention is intended to provide an antibody or an antigen-binding fragment thereof that binds to the CNTN4 protein to neutralize an immune escape mechanism of CNTN4.

The present invention is also intended to provide a composition for preventing or treating diseases, such as cancer, caused by a decrease in T cell activity, by using the antibody or antigen-binding fragment thereof to block the immune escape mechanism of CNTN4 and activate T cells.

The present invention is also intended to provide a composition for analyzing or detecting a CNTN4 protein using the antibody or antigen-binding fragment thereof.

Solution to Problem

The present invention provides an anti-CNTN4 antibody or an antigen-binding fragment thereof, which specifically binds to a CNTN4 protein. The antibody or antigen-binding fragment specifically binds to a CNTN4 protein, for example, a human or mouse CNTN4 protein, to neutralize an immune escape mechanism of CNTN4. Accordingly, the antibody or antigen-binding fragment of the present invention may increase the activity of T cells, such as CD4+ T cells or CD8+ T cells, which have been inhibited by CNTN4.

In an embodiment, the present invention provides an anti-CNTN4 antibody or an antigen-binding fragment thereof comprising:

- a light chain variable region comprising an amino acid sequence of SEQ ID NO: 1; and
- a heavy chain variable region comprising an amino acid sequence of SEQ ID NO: 2.

In an embodiment, the antibody of the present invention may be a monoclonal antibody.

In another embodiment, the present invention provides a nucleic acid molecule encoding the antibody or antigen-binding fragment thereof and a recombinant expression vector including the nucleic acid molecule.

The present invention also provides a composition for preventing or treating cancer, the composition comprising the antibody or antigen-binding fragment thereof as an active ingredient. The pharmaceutical composition may be used in combination with an additional anticancer agent, such as an immune checkpoint inhibitor or a chemotherapeutic agent, or may be used in combination with radiation therapy.

The present invention also provides a composition for analyzing or detecting a CNTN4 protein, the composition comprising the antibody or antigen binding fragment thereof.

Advantageous Effects of Invention

The inventors of the present invention have confirmed that the CNTN4 protein is an immune checkpoint protein, and the degree of immune avoidance due to the inhibition of T cell activity is stronger than that of PD-L1 known as a conventional immune checkpoint protein.

In addition, the novel anti-CNTN4 antibody or antigen-binding fragment thereof of the present invention activates T-cells by blocking the immune escape mechanism of CNTN4, and thus can be effectively used to prevent or treat diseases caused by a decrease in T-cell activity, particularly, cancer. Therefore, when the anti-CNTN4 antibody of the present invention is used, an excellent anticancer effect may be exhibited with respect to cancer for which a therapeutic effect cannot be achieved with existing immunotherapy.

BRIEF DESCRIPTION OF DRAWINGS

FIG. 1 is a graph showing the degree to which CNTN4 inhibits the activity of human T cells compared to PD-L1.

FIG. 2 shows amino acid sequences of light and heavy chain variable regions of the monoclonal antibody produced according to Example 2 (hAb-1 light chain variable region (VL): SEQ ID NO: 1, and hAb-1 heavy chain variable region (VH): SEQ ID NO: 2.

FIG. 3 shows the binding ability of a monoclonal antibody hAb-1 to antigen proteins, human CNTN4 and mouse CNTN4.

FIG. 4 shows whether the monoclonal antibody hAb-1 competitively binds with the CNTN4 receptor for CNTN4.

FIG. 5 shows that the monoclonal antibody hAb-1 effectively neutralizes the CNTN4 protein to proliferate T cells.

FIG. 6 shows the antitumor efficacy of the monoclonal antibody hAb-1 in a CT26 syngeneic mouse model of colorectal cancer according to Example 6. The dotted line indicates that drugs were treated on day 0, day 3, day 6, and day 9 in each experimental group. Statistical significance was determined with multiple comparison test using two-way ANOVA test (*P<0.05, P<0.01, *P<0.001, ****P<0.0001 versus group 1 (hIgG4))).

FIGS. 7 to 10 show the efficacy of the monoclonal antibody hAb-1 for increasing the splenic T cell activity in a CT26 syngeneic mouse model of colorectal cancer according to Example 7. FIGS. 7 to 9 show the percentage of CD4+ T cells to CD45+ cells (i.e., CD3+CD4+/CD45+), the percentage of CD8+ T cells to CD45+ cells (i.e., CD3+CD8+/CD45+), and the percentage of cells that secrete IFNγ among CD8+ T cells (i.e., IFNγ/CD8+), respectively. FIG. 10 shows a degree of reduction in tumor volume in each mouse used in the analysis.

FIG. 11 shows the antitumor efficacy of the monoclonal antibody hAb-1 in an EMT6 syngeneic mouse model of mammary cancer according to Example 8. The dotted line indicates that drugs were treated on day 0, day 3, day 6, and day 9 in each experimental group. Statistical significance was determined with multiple comparison test using two-way ANOVA test (*P<0.05, P<0.01, *P<0.001, ****P<0.0001 versus group 1 (hIgG4))).

FIGS. 12 and 13 show the efficacy of the monoclonal antibody hAb-1 for increasing the splenic T cell activity in an EMT6 syngeneic mouse model of mammary cancer according to Example 9. FIGS. 12 and 13 show the percentage of cells that secrete IFNγ among CD4+ T cells and CD8+ T cells (i.e., IFNγ/CD4+ and IFNγ/CD8+), respectively.

FIGS. 14 and 15 show the efficacy of the monoclonal antibody hAb-1 for increasing the splenic T cell activity in an LLC-1 syngeneic mouse model of lung cancer according to Example 10. FIG. 14 shows the percentage of cells that secrete IFNγ among CD3+ T cells (i.e., IFNγ/CD3+). FIG. 15 shows a degree of reduction in tumor volume in each mouse used in the analysis.

BEST MODE FOR CARRYING OUT THE INVENTION

Anti-CNTN4 Antibody or Antigen-binding Fragment Thereof

The present invention provides an anti-CNTN4 antibody or an antigen-binding fragment thereof, which specifically binds to a CNTN4 protein.

In an embodiment, the anti-CNTN4 antibody or antigen-binding fragment thereof of the present invention comprises: a light chain variable region comprising an amino acid sequence of SEQ ID NO: 1; and a heavy chain variable region comprising the amino acid sequence of SEQ ID NO: 2.

As used herein, that a light chain or heavy chain variable region comprises a specific amino acid sequence means that the light chain or heavy chain variable region comprises the entire amino acid sequence, has the entire amino acid sequence, or consists of the amino acid sequence.

In an example, the antibody or antigen-binding fragment thereof comprises a light chain variable region having the amino acid sequence of SEQ ID NO: 1, and a heavy chain variable region having the amino acid sequence of SEQ ID NO: 2. In another example, the antibody or antigen-binding fragment thereof comprises a light chain variable region consisting essentially of the amino acid sequence of SEQ ID NO: 1, and a heavy chain variable region consisting essentially of the amino acid sequence of SEQ ID NO: 2.

As another example, the antibody or antigen-binding fragment thereof comprises a light chain variable region consisting of the amino acid sequence of SEQ ID NO: 1, and a heavy chain variable region consisting of the amino acid sequence of SEQ ID NO: 2.

As used herein, the terms "comprising," "comprise," or modified words thereof refer to an open meaning. As an example, an antibody or antigen-binding fragment thereof comprising the amino acid sequence listed may include additional amino acid sequences not listed, whether essential or not.

As used herein, the term "consisting essentially of" or a modified phrase thereof includes any of the mentioned elements, and permits the presence of elements that do not substantially affect the basic and novel or functional characteristics of the embodiment. As an example, an antibody or antigen-binding fragment thereof consisting essentially of the amino acid sequence listed may include a substitution of one or more amino acid residues that do not substantially affect the characteristics of the antibody or fragment thereof.

As used herein, the term "consisting of" or a modified phrase thereof refers to the case where respective components as described herein do not permit any element that is not recited or listed in that description of the embodiment.

The term "antibody" as used herein refers to an immunoglobulin molecule capable of specifically binding to a target, such as a carbohydrate, polynucleotide, lipid, polypeptide, protein, etc., through at least one antigen recognition site, located in the variable region of the immunoglobulin molecule. The term "antibody" herein encompasses not only an intact polyclonal or monoclonal antibody, but also an antigen-binding fragment thereof, and a fusion protein including an antibody fragment, and any other modified configuration of the immunoglobulin molecule that includes an antigen recognition site.

An antibody includes five classes of immunoglobulin (Ig)M, IgD, IgG, IgA, and IgE, comprising heavy chains made from the heavy chain constant region genes μ, δ, γ, α, and ε, respectively.

The light chain and the heavy chain of the antibody are divided into variable regions having different amino acid sequences for each antibody and constant regions having the same amino acid sequence, and the heavy chain constant regions comprise CH1, H (hinge), CH2, and CH3 domains. Each domain consists of two ß-sheets and an intramolecular disulfide bond is linked therebetween.

An antibody comprising a light chain variable region consisting of the amino acid sequence of SEQ ID NO: 1, and a heavy chain variable region consisting of the amino acid sequence of SEQ ID NO: 2 is referred to as “antibody hAb-1” herein.

In an embodiment, the antibody of the present invention may be a monoclonal antibody. In another embodiment, the antibody of the present invention may be a chimeric antibody, a humanized antibody, or a human antibody.

As used herein, the term “chimeric antibody” refers to antibodies in which the variable region sequences are derived from one species and the constant region sequences are derived from another species, such as an antibody in which the variable region sequences are derived from a mouse antibody and the constant region sequences are derived from a human antibody.

As used herein, the term “humanized antibody” refers to antibodies in which CDR sequences derived from the germline of another mammalian species, such as a mouse, have been grafted onto human framework sequences. The framework sequences may further be remodified via back mutation, for example.

As used herein, the term “human antibody” refers to antibodies in which both frameworks and CDR regions comprise variable regions derived from human immunoglobulin sequences. The constant regions of antibodies are also derived from human immunoglobulin sequences.

As used herein, the term “antigen-binding fragment” or “antibody fragment” refers to antigen-binding fragments and analogues of an antibody, typically comprising at least a portion of the antigen binding or variable regions (e.g. one or more CDRs) of the parental antibody. An antibody fragment retains at least some of the binding specificity of the parent antibody. Examples of antibody fragments include, but are not limited to, Fab, Fab', Fab'-SH, Fv, F(ab')2 fragments, single-chain antibodies scFv, single domain antibodies, diabodies (dAbs), or linear antibodies.

Specifically, the Fab fragment refers to a monovalent fragment composed of VL, VH, CL, and CH1 domains.

The Fab' fragment differs from the Fab fragment in that several residues are added at the carboxyl terminus of the CH1 domain comprising at least one cysteine from the antibody hinge region.

The Fab'-SH refers to a Fab' in which the cysteine residue of the constant domain has a free thiol group.

The F(ab')2 antibody fragment is generated as a pair of Fab' fragments via a hinge cysteine between the Fab' fragments.

The Fv is a minimum antibody fragment containing a complete antigen-recognition site and -binding site. This fragment consists of a dimer of one heavy chain variable region and one light chain variable region in tight, non-covalent association. From the folding of these two regions emanate six hypervariable loops (three loops each from the heavy and light chain) that contribute the amino acid residues for antigen-binding and confer antigen binding specificity to the antibody. However, even a single variable region has the ability to recognize and bind antigen, although at a lower affinity than the entire binding site.

The single chain antibody scFv is an antibody fragment that comprises VH and VL antibody domains linked into a single polypeptide chain. Preferably, the scFv polypeptide further includes a polypeptide linker between the VH and VL domains that enables the scFv to form the desired structure for antigen binding. The scFv polypeptide herein is also referred to scFv antibody fragment, antigen-binding fragment scFv, scFv antibody, antibody scFv, or simply scFv.

The diabodies refer to small antibody fragments prepared by constructing scFv fragments using short linkers (about 5-10 residues) between the VH and VL domains such that inter-chain but not intra-chain pairing of the V domains is achieved, resulting in a bivalent fragment, i.e., a fragment having two antigen-binding sites. Bispecific diabodies are heterodimers consisting of two “crossover” scFv fragments in which the VH and VL domains of the two antibodies are present on different polypeptide chains.

The anti-CNTN4 antibody or antigen-binding fragment thereof of the present invention may specifically bind to an CNTN4 protein, preferably a human or mouse CNTN4 protein.

As used herein, the term “specifically binds to” or “specific for” refers to measurable and reproducible interactions such as binding between a target and an antibody, which is determinative of the presence of the target in the presence of a heterogeneous population of molecules including biological molecules. For example, an antibody that specifically binds to a specific target (e.g., an epitope) is an antibody that binds this target with greater affinity, avidity, more readily, and/or with greater duration than it binds to other targets.

As used herein, the term “specifically binding to a human CNTN4 protein” may refer to an antibody that binds to a human CNTN4 protein with a dissociation constant (Kd) of $1\times10^{-7}$ M or less, or preferably $5\times10^{-8}$ M or less. Accordingly, the anti-CNTN4 antibody or antigen binding fragment thereof of the present invention may bind to human CNTN4 protein with a dissociation constant (Kd) of $1\times10^{-7}$ M or less, preferably $5\times10^{-8}$ M or less.

As used herein, the term “Kd” refers to an equilibrium dissociation constant of a particular antibody-antigen interaction, wherein the constant has a unit of M. The Kd values for antibodies can be determined using methods widely established in the art. A preferred method for determining the Kd value of an antibody is by using surface plasmon resonance (SPR), preferably using a biosensor system such as a Biacore® system.

In an embodiment, the anti-CNTN4 antibody or antigen-binding fragment thereof of the present invention is single specific and specifically binds to a single epitope, i.e., a CNTN4 protein.

In another embodiment, the anti-CNTN4 antibody or antigen-binding fragment thereof of the present invention is a multispecific antibody molecule, such as a bispecific or trispecific antibody molecule. The multispecific antibody molecule includes a plurality of variable regions, each variable region having binding specificity to a different epitope. In an embodiment, the first variable region of the bispecific antibody molecule has a first binding specificity to a first epitope, e.g., a CNTN4 protein, and the second variable region has a second binding specificity to a second epitope, e.g., a target protein other than the CNTN4 protein (e.g., including but not limited to CTLA-4, PD-1, or PD-L1). In one specific embodiment, the bispecific antibody molecule specifically binds to CNTN4; and any one of CTLA-4, PD-1 or PD-L1. In another embodiment, any combination of the above molecules can be prepared with a multispecific antibody molecule, e.g., a trispecific antibody including a first binding specificity to CNTN4, and second and third binding specificities to at least two of CTLA-4, PD-1 or PD-L1. The multispecific antibody molecule of the present invention may be prepared using standard molecular biological techniques known to those skilled in the art (e.g., recombinant DNA and protein expression technology).

In another embodiment, the anti-CNTN4 antibody or antigen-binding fragment have a thereof of the present invention may form an antibody-drug conjugate (ADC). As used herein, the term "antibody-drug conjugate" or "ADC" may be represented by the formula M-[L-D]n, wherein M represents an antibody molecule, i.e., an anti-CNTN4 antibody of the present invention or an antigen-binding fragment thereof, L is an optional linker or linker unit, D is a suitable drug or prodrug, and n is an integer from about 1 to about 20. The drug included in the ADC may be appropriately selected according to therapeutic or diagnostic use, as long as the drug does not interfere with specific binding of the antibody of the present invention. In an embodiment, the drug includes, but is not limited to, a cytotoxic agent (e.g., a chemotherapeutic agent), a prodrug converting enzyme, a radioactive isotope or compound, or a toxin. Drugs and linkers that may be included in the ADC and preparation methods thereof may be according to methods known in the art.

The anti-CNTN4 antibody or antigen-binding fragment thereof of the present invention exhibits excellent competitive binding ability to the CNTN-4 protein even in the presence of CNTN-4 receptors. Accordingly, the anti-CNTN4 antibody or antigen-binding fragment thereof of the present invention may specifically bind to the CNTN-4 protein to substantially equal extent even when the CNTN-4 receptors are present in the body.

In another embodiment, the anti-CNTN4 antibody or antigen-binding fragment thereof of the present invention binds to a CNTN4 protein (e.g., a human or mouse CNTN4 protein) with an EC50 of 5 nM or less, preferably 3 nM or less, more preferably 2 nM, and even more preferably 1 nM or less as determined by ELISA assay.

As used herein, the term "EC50" is a term related to an in vitro or in vivo assay using an antibody, which refers to the concentration of an antibody that induces 50% of the maximum response, i.e., an intermediate response between the maximum response and baseline.

Nucleic Acid Molecule and Vector

Another aspect of the present invention relates to a nucleic acid molecule encoding the anti-CNTN4 antibody or antigen-binding fragment thereof of the present invention.

The nucleic acid may be present in whole cells, in a cell lysate, or in a specifically purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art.

The nucleic acid of the present invention may be, for example, DNA or RNA and may or may not contain intronic sequences. In a preferred embodiment, the nucleic acid is a cDNA molecule.

In an embodiment, the nucleic acid molecule of the present invention encodes the light chain region, the heavy chain region, or both the light chain and the heavy chain regions of the anti-CNTN4 antibody or antigen-binding fragment thereof of the present invention, and preferably encodes the light chain variable region, the heavy chain variable region, or both the light chain and the heavy chain variable regions. In an embodiment, the nucleic acid molecule of the present invention encodes a light chain variable region comprising SEQ ID NO: 1, and/or encodes a heavy chain variable region comprising SEQ ID NO: 2, or encodes an antibody hAb-1.

Once DNA fragments encoding the VL and/or VH regions are obtained, such DNA fragments can be further manipulated by standard recombinant DNA techniques, for example, to thus convert the variable region genes to full-length antibody chain genes, to Fab fragment genes or to a scFv gene. In these manipulations, a VL- or VH-encoding DNA fragment is operatively linked to another DNA fragment encoding another protein, for example, an antibody constant region or a flexible linker. As used herein, the term "operatively linked" means that the two DNA fragments are joined such that the amino acid sequences encoded by the two DNA fragments remain in-frame.

The isolated DNA encoding the VH region can be converted to a full-length heavy chain gene by operatively binding the VH-encoding DNA to another DNA molecule encoding heavy chain constant regions (CH1, CH2 and CH3). The heavy chain constant region may be an IgG1, IgG2, IgG3, IgG4, IgA, IgE, IgM, or IgD constant region.

For a Fab fragment heavy chain gene, the VH-encoding DNA can be operatively linked to another DNA molecule encoding only the heavy chain CH1 constant region.

To create a scFv gene, the VL- and VH-encoding DNA fragments are operatively linked to another fragment encoding a flexible linker, e.g., encoding the amino acid sequence (Gly4-Ser)3, such that the VL and VH sequences can be expressed as a contiguous single-chain protein, with the VL and VH regions joined by the flexible linker.

The nucleic acid sequences of the present invention, such as RNA or DNA, may be isolated from a variety of sources, genetically engineered, amplified, and/or expressed recombinantly. Any recombinant expression system can be used, including, in addition to bacterial, e.g., yeast, insect or mammalian systems. For example, the manipulation of nucleic acids, such as subcloning into expression vectors, labeling probes, sequencing, and hybridization may be performed as known in the art.

Accordingly, the present invention provides a recombinant expression vector including the nucleic acid molecule.

As used herein, the term "vector" refers to a DNA molecule capable of self-replication in prokaryotic and/or eukaryotic cells and is used interchangeably with a recombinant vector, a cloning vector, or an expression vector, which is generally used as a carrier for delivering genes or DNA fragments to cells and the like. The vectors generally include, but are not limited to, an origin of replication that can be replicated in prokaryotic and/or eukaryotic cells, a selection marker gene that can confer resistance to a particular conditions/substances such as antibiotic degrading enzymes, a promoter capable of transcription of genes in eukaryotic or prokaryotic cells, and translatable sequences.

One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors).

Preparation of Antibody or Antigen-Binding Fragment thereof

The antibody or antigen-binding fragment thereof of the present invention may be prepared according to conventionally known methods.

In an embodiment, in order to express an antibody or an antigen binding fragment thereof, a recombinant expression vector including the nucleic acid molecule coding a partial or full length light chain and heavy chain is transfected into a host cell. As a method of transfection, techniques commonly used for the introduction of exogenous DNA into prokaryotic or eukaryotic host cells may be used, including, but not limited to, for example, electroporation, calcium phosphate precipitation, DEAE-dextran transfection, and the like.

The host cells for the expression of the antibody or antigen-binding fragment thereof of the present invention may be prokaryotic cells or eukaryotic cells, and preferably may be eukaryotic cells, particularly, mammalian cells.

Examples of mammalian host cells include, but are not limited to, human embryonic kidney cells (e.g., 293 cells subcloned for growth in suspension culture or 293 cells), Expi293F™ cells, CHO cells, baby hamster kidney cells (e.g., BHK, ATCC CCL 10), mouse sertoli cells (e.g., TM4 cells), monkey kidney cells (e.g., CV1 ATCC CCL 70), African green monkey kidney cells (e.g., VERO-76, ATCC CRL-1587), human cervix carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TRI cells, MRC 5 cells, FS4 cells, a human hepatoma line (e.g., Hep G2), and myeloma cells (e.g., NS0 and Sp2/0 cells).

The transformed host cells may be cultured in suitable media to produce a polypeptide of a heavy chain, a light chain, or an antigen-binding fragment thereof of the antibody according to the present invention from the recombinant expression vector introduced into the host cells. The composition of the media for culturing the host cells, the culturing condition, the culturing time, and the like may be appropriately selected according to a method commonly used in the art. For example, commercially available media such as Ham's F10 (Sigma-Aldrich Co., St. Louis, MO), minimal essential media (MEM, Sigma-Aldrich Co.), RPMI-1640 (Sigma-Aldrich Co.), and Dulbecco's modified eagle medium (DMEM, Sigma-Aldrich Co.) may be used, but are not limited thereto. When necessary, hormones, growth factors, salts, buffers, nucleotides, antibiotics, trace elements, and the like may be additionally added to the media.

Antibodies or antigen-binding fragments thereof produced in the host cell may be obtained through a process such as purification. The obtaining method may be appropriately selected in consideration of the characteristics of the polypeptide of the antibodies or antigen-binding fragments thereof produced in the host cell, the characteristics of the host cell, the expression method, or whether to target the polypeptide. For example, the antibodies or antigen-binding fragments thereof secreted to the culture media may be recovered by a method of obtaining media in which host cells are cultured and centrifuging the media to remove impurities. In addition, the obtained antibodies may further undergo a process of further removing impurities through a method such as chromatography, filtration by a filter or the like, or dialysis, and concentrating the antibodies, and a purification method of two steps, for example, a method of primarily purifying through protein A affinity chromatography and then secondarily purifying through cation ion exchange chromatography may be used.

Uses and Methods

The antibody or antigen-binding fragment thereof of the present invention recovers an immune response inhibited by the binding of the CNTN4 protein. The CNTN4 protein inhibits the proliferation of T cells, particularly, CD4+ T cells and CD8+ T cells. The antibody or antigen-binding fragment thereof of the present invention may be used to treat diseases related to immunosuppression by specifically binding to the CNTN4 protein to thus increase T cell activity, particularly the activity of CD4+ T cells or CD8+ T cells.

In an embodiment, the antibody or antigen-binding fragment thereof of the present invention increases T cell activity.

As used herein, the term "T cell" refers to a type of leukocytes that can be distinguished from other leukocytes by the presence of a T cell receptor on the cell surface. There are subsets of several T cells, including, but not limited to, T helper cells (also referred to as TH cells or CD4+ T cells) and subtypes (including TH1, TH2, TH3, TH17, TH9, and TFH cells); cytotoxic T cells (also referred to as TC cells, CD8+ T cells, cytotoxic T lymphocytes, T-killer cells, killer T cells), memory T cells and subtypes (central memory T cells (TCM cells), effector memory T cells (TEM and TEMRA cells), and resident memory T cells (TRM cells)), regulatory T cells (also referred to as Treg cells or suppressor T cells), and subtypes (including CD4+ FOXP3+ Treg cells, CD4+ FOXP3− Treg cells, Tr1 cells, Th3 cells, and Treg17 cells); natural killer T cells (also known as NKT cells), mucosal associated invariant T cells (MAIT), and gamma delta T cells (γδ T cells) (including Vγ9/Vδ2 T cells). In the present invention, preferably, the T cells are CD4+ T cells or CD8+ T cells.

As used herein, the term "T cell activation" refers to a cellular process in which mature T cells, which express antigen-specific T cell receptors on their surfaces, recognize their cognate antigens and respond by the mature T cells entering the cell cycle, secreting cytokines or lytic enzymes, and initiating to perform effector functions of T cells.

Accordingly, the antibody or antigen-binding fragment thereof of the present invention may activate T cells, particularly CD4+ T cells or CD8+ T cells. In an embodiment, the antibody or antigen-binding fragment thereof of the present invention may increase the proliferation of T cells that have been inhibited by CNTN4. The antibody or antigen-binding fragment thereof of the present invention has excellent ability to neutralize CNTN4.

Accordingly, the present invention relates to the induction of T-cell activation by using an anti-CNTN4 antibody or an antigen-binding fragment thereof. In an embodiment, the present invention provides a method for inducing or enhancing T cell activation, the method including administering, to a subject, an effective amount of an anti-CNTN4 antibody or an antigen-binding fragment thereof. In another embodiment, the present invention provides a use of an anti-CNTN4 antibody or an antigen-binding fragment thereof for inducing or enhancing T cell activation.

In another embodiment, the present invention provides a pharmaceutical composition for inducing or enhancing T cell activation, the composition comprising an anti-CNTN4 antibody or an antigen-binding fragment thereof.

In another embodiment, the present invention relates to the prevention, amelioration, or treatment of immunosuppression-related diseases by using an anti-CNTN4 antibody or an antigen-binding fragment thereof.

In an embodiment, the present invention provides a method for preventing, ameliorating or treating immunosuppression-related diseases, the method comprising administering, to a subject, an effective amount of an anti-CNTN4 antibody or an antigen-binding fragment thereof.

In another embodiment, the present invention provides a use of an anti-CNTN4 antibody or an antigen-binding fragment thereof for preventing, ameliorating or treating immunosuppression-related diseases.

In another embodiment, the present invention provides a pharmaceutical composition for the prevention, amelioration, or treatment of immunosuppression-related diseases, the pharmaceutical composition comprising an anti-CNTN4 antibody or an antigen-binding fragment thereof.

As used herein, the term “subject” is meant to include both human and non-human animals. Non-human animals include all vertebrates, e.g., mammals and non-mammals, including non-human primates, sheep, dogs, cats, cattle, horses, chickens, amphibians and reptiles, but, for example, non-human primates, sheep, dogs, cats, cattle, and horses are preferred. A preferred subject is a human in need of immune response activation or enhancement.

Preferably, the anti-CNTN4 antibody or antigen-binding fragment thereof of the present invention blocks the binding of the CNTN4 protein, thereby activating T cells and/or enhancing an immune response to cancer cells in a cancer patient, and thus may inhibit the growth of cancer cells in vivo, and therefore may be effectively used to prevent, ameliorate, or treat cancer.

Preferred cancers of which growth may be inhibited when the antibodies of the present invention are used include cancers typically responsive to immunotherapy. For example, cancers in the present invention include, but are not limited to, gastric cancer, pancreatic cancer, endometrial cancer, liver cancer, gallbladder cancer, prostate cancer (e.g., hormone refractory prostate adenocarcinoma), melanoma (e.g., metastatic malignant melanoma or malignant melanoma in the skin and eye), kidney cancer (e.g., clear cell carcinoma), breast cancer (e.g., invasive breast cancer, non-invasive breast cancer), colorectal cancer, rectal cancer, colon cancer, and lung cancer (e.g., non-small cell lung cancer). Specific examples of the cancers may include gastric cancer, pancreatic cancer, endometrial cancer, liver cancer, gallbladder cancer, prostate cancer, or melanoma. In addition, a subject to be treated of the present invention includes refractory or recurrent malignancies of which growth may be inhibited when the antibodies of the present invention are used.

Examples of other cancers that may be treated using the methods of the present invention include bone cancer, skin cancer, head and neck cancer, uterine cancer, ovarian cancer, rectal cancer, cancer of the anal region, testicular cancer, uterine cancer, carcinoma of the fallopian tubes, cervical cancer, vaginal cancer, female vulva cancer, Hodgkin’s disease, non-Hodgkin’s lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, bladder cancer, kidney cancer, ureteral cancer, carcinoma of the renal pelvis, neoplasm of the central nervous system (CNS), primary CNS lymphoma, tumor angiogenesis, spinal axis tumor, brain stem glioma, pituitary adenoma, Kaposi’s sarcoma, epidermoid cancer, squamous cell cancer, T-cell lymphoma, or a combination of these cancers.

The antitumor activity of the anti-CNTN4 antibody or antigen-binding fragment thereof of the present invention can be tested in vivo. To this end, a syngeneic tumor model known in the art, for example, a CT26 tumor model of colorectal cancer, an EMT6 tumor model of mammary cancer, or an LLC-1 tumor model of lung cancer, may be used.

In another embodiment, the cancers may be cancers that express CNTN4.

In another embodiment, the cancers may be refractory or resistant to conventional immune checkpoint inhibitors (e.g., resistant to PD-1 pathway inhibitors, PD-1 pathway inhibitors, or CTLA-4 pathway inhibitors).

The antibody or antigen-binding fragment of the present invention may be used alone or in combination with other anticancer therapies. Other anticancer therapies may include, for example, standard cancer therapies (e.g., chemotherapies, radiotherapies, or surgery); or other anticancer agents, such as cytotoxic, cytostatic, anti-angiogenic or antimetabolite agents, tumor targeted agents, immune stimulating or immune modulating agents, or antibodies conjugated to cytotoxic, cytostatic, or other toxic agents, immune checkpoint inhibitors, and the like.

Preferably, the antibody or antigen-binding fragment of the present invention may be used in combination with other anticancer agents such as immune checkpoint inhibitors, chemotherapeutic agents, or radiotherapies. The immune checkpoint inhibitors may be, for example, anti-CTLA-4 antibodies (e.g., ipilimumab), anti-PD-1 antibodies (e.g., pembrolizumab, nivolumab), or anti-PD-L1 antibodies (e.g., atezolizumab, avelumab, durvalumab). The chemotherapeutic agents include, but are not limited to, alkylating agents, antimetabolites, kinase inhibitors, spindle poison plant alkaloids, cytotoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, luteinizing hormone-releasing hormone agonists, anti-androgens, aromatase inhibitors, EGFR inhibitors, VEGF inhibitors, anti-sense oligonucleotides that inhibit expression of genes implicated in abnormal cell proliferation or tumor growth.

Specific examples of chemotherapeutic agents of the present invention include gemcitabine, vinorelbine, etoposide (VP-16), platinum analogs such as cisplatin or carboplatin, taxoids such as paclitaxel, albumin-binding paclitaxel, and doxetaxel, or the like. Other cancer therapeutic agents include probiotics exhibiting anticancer effects, such as *Lactococcus lactis* GEN3013 strain (KCTC13426BP), *Lactococcus lactis* GEN3033 strain (KCTC13684BP), *Bifidobacterium bifidum* MG731 strain (KCTC13452BP), and the like.

When the antibody or antigen-binding fragment of the present invention is used in combination with other anticancer agents, these may be administered separately or may be applied in the form of a combination product in which a plurality of active ingredients are present in a single pharmaceutical formulation. When these are administered as separate formulations, the two formulations may be administered sequentially or simultaneously. For simultaneous administration, these are given together to the patient. For sequential administration, these may be given at a time interval that is not long, for example, these formulations may be administered to a patient within a period of 12 hours or less, or 6 hours or less.

In an embodiment, the present invention provides a method of preventing, ameliorating, or treating immunosuppression-related diseases, such as cancer, the method including administering, to a subject, an effective amount of an anti-CNTN4 antibody or an antigen-binding fragment thereof in combination with an additional anticancer agent.

The embodiment includes not only simultaneously administering a single composition containing an anti-CNTN4 antibody or an antigen-binding fragment together with an additional anticancer agent to a patient in need thereof, but also simultaneously or sequentially administering compositions separately and respectively containing the anti-CNTN4 antibody or antigen-binding fragment and the additional anticancer agent to a patient in need thereof.

In another embodiment, the present invention provides a use of an anti-CNTN4 antibody or antigen-binding fragment thereof for using in combination with an additional anticancer agent for preventing, ameliorating, or treating immunosuppression-related diseases, such as cancer.

In another embodiment, the present invention provides a pharmaceutical composition or combination for preventing, ameliorating, or treating immunosuppression-related diseases, such as cancer, the composition or combination comprising an anti-CNTN4 antibody or an antigen-binding fragment thereof, and an additional anticancer agent. The pharmaceutical composition or combination herein comprising an anti-CNTN4 antibody or an antigen-binding fragment thereof, and an additional anticancer agent, include not only the case where the two components are physically present together in the form of a single formulation, but also the case where the two components are administered simultaneously or sequentially in separate formulations, wherein the two drugs may be provided separately or together in a single kit. Accordingly, the present invention provides a kit for preventing, ameliorating, or treating immunosuppression-related diseases, such as cancer, the kit comprising an anti-CNTN4 antibody or an antigen-binding fragment thereof and an additional anticancer agent.

The additional anticancer agent may preferably be immune checkpoint inhibitors, more preferably, anti-CTLA-4 antibodies (e.g., ipilimumab), anti-PD-1 antibodies (e.g., pembrolizumab and nivolumab), or anti-PD-L1 antibodies (e.g., atezolizumab, avelumab, and durvalumab).

Another preferred additional anticancer agent may include chemotherapeutic agents such as gemcitabine, vinorelbin, etoposide (VP-16), platinum analogs such as cisplatin or carboplatin, taxoids such as paclitaxel, albumin-binding paclitaxel, or doxetaxel.

Another preferred additional anticancer therapy used with the antibody or antigen-binding fragment thereof of the present invention may include radiotherapy.

The present invention also provides a method for detecting the presence of the CNTN4 protein in a sample or measuring the amount of the anti-CNTN4 antibodies by using the anti-CNTN4 antibody or antigen-binding fragment thereof as an active ingredient. The method includes bringing the antibody or antigen-binding fragment thereof into contact with a sample and a control sample under the conditions under which the antibody or antigen-binding fragment thereof can bind to the CNTN4 protein to form a complex. Then, whether the complex has been formed is detected, wherein a difference in the degree of complex formation between the samples compared to the control sample is evidence that human blood antigens are present in the sample (e.g., blood).

Accordingly, the present invention provides a composition for diagnosing cancer, the composition comprising the anti-CNTN4 antibody or antigen-binding fragment thereof.

Pharmaceutical Composition

The present invention provides a pharmaceutical composition comprising an anti-CNTN4 antibody or an antigen-binding fragment thereof. The composition may contain inactive ingredients, that is, pharmaceutically acceptable excipients (see Handbook of Pharmaceutical Excipients, etc.). Compositions of therapeutic and diagnostic formulations may be prepared in the form of, for example, freeze-dried powder, slurry, aqueous solution or suspension by mixing the formulations with physiologically acceptable carriers, excipients, or stabilizers.

Suitable route of administration includes parenteral administration, such as intramuscular, intravenous, or subcutaneous administration. Administration of the antibodies used in the pharmaceutical composition of the present invention or used to practice the methods of the present invention may be carried out by a variety of conventional methods such as topical application, or intradermal, subcutaneous, intraperitoneal, parenteral, intraarterial, or intravenous injection. In an embodiment, the antibody of the present invention is administered intravenously or subcutaneously.

Hereinafter, the present invention will be described in more detail with reference to Examples. It will be apparent to those skilled in the art that these Examples are only intended to describe the present invention in more detail, and the scope of the present invention is not limited by these Examples according to the subject matter of the present invention.

Modes for the Invention

Example 1: Confirmation of CNTN4's Ability to Inhibit Human T Cell Activity

In this example, the degree to which CNTN4 inhibits the activity of human T cells was confirmed compared to PD-L1, which is known as an immune checkpoint protein.

α-CD3 antibodies at a concentration of 4 μg/mL and human PD-L1 and human CNTN4 recombinant proteins each at concentrations of 50, 100, 150, and 200 nM were prepared into a final 50 μL and put into a 96-well plate. The 96-well plate was incubated at 37° C. for about 16 hours while being careful not to generate bubbles at the bottom of the 96-well plate.

50 mL of blood (contained in a blood collection tube treated with sodium heparin) per donor and PBS were mixed at a ratio of 1:1, 15 mL of Ficoll was previously contained in a 50-mL tube, and 30 mL of diluted blood was carefully placed thereon and stacked such that the Ficoll layer and the blood layer were separated. Centrifugation (acceleration and deceleration speeds set to 0) was performed for 25 minutes at 1,800 rpm and 20° C., and the supernatant was removed such that a white buffy layer did not rise. The buffy layer was transferred to a new 50-mL tube, and the tube was filled to 50 mL with PBS, and centrifuged for 5 minutes at 1,800 rpm and 4° C. 10 mL of 1×RBC lysis buffer was added, dissolved well, and left at room temperature for 5 minutes. After filling up to 50 mL with PBS, centrifugation was performed for 5 minutes at 1,800 rpm and 4° C., the supernatant was removed, and the pellets were dissolved with PBS, and cells (PBMC) were then observed through a microscope and the number of cells was calculated.

1,000 μL of MACS buffer per $2\times10^8$ PBMC cells obtained in the above experiment was added, followed by resuspension. The solution was divided into two halves, one half of which was put into a CD4 tube, and one half of which was put into a CD8 tube. 50 μL of antibody cocktail per $1\times10^8$ PBMCs of each group was resuspended and stored at room temperature for 10 minutes. 100 μL of anti-biotin microbeads per $1\times10^8$ PBMCs was resuspended and stored at room temperature for 10 minutes. Meanwhile, MACS magnetic field was disinfected and placed in a clean bench, and two LS columns (for CD4 and CD8) were installed. After flowing 3 mL of MACS buffer into each column, the buffer passing through each column was discarded. The cells of each group after the reaction was completed were loaded onto two LS columns mounted on the magnetic field, respectively. When there was no more cell solution falling down, 3 mL of MACS buffer was allowed to flow into each column. Thereafter, cells in a solution that fell from each column were observed through a microscope and the number of cells was calculated.

18 μL of DMSO was added to 50 μg of CFSE and pipetted to make a concentration of 5 mM and use the cells. 1 mL of MTM media was added to the CD4 cells and CD8 cells obtained in the above experiment, CFSE was added to reach a final concentration of 5 μM, suspended, and then stored in a water bath at 37 ° C. for 10 minutes. The solution was centrifuged at 1,800 rpm and 4° ° C. for 5 minutes, and the supernatant was removed. Then, 1 mL of MTM media was added thereto and resuspended, and then centrifuged again at 1,800 rpm and 4° C. for 5 minutes, and the supernatant was removed. Finally, the cells were resuspended with MTM media to reach $2\times10^5$ cells/200 μL per well to be used in the experiment.

The incubated plate was washed twice with 200 μL of PBS, 200 μL of T cells per well were added, and then stored in a 5% $CO_2$ incubator at 37° ° C. for 3 days. After 3 days, T cells were obtained and transferred to a FACS tube, and the degree of cells differentiated, which are stained with CFSE, was observed using a FACS instrument. The results are shown in FIG. 1.

As shown in FIG. 1, it was confirmed that the PD-L1 and CNTN4 recombinant proteins inhibit the proliferation of $CD4^+$ T cells and $CD8^+$ T cells. This result was commonly observed in two donors, and in particular, comparing the treatment of 200 nM of CNTN4 with the treatment of 200 nM of PD-L1, it may be seen that the proliferation of T cells in the CNTN4 treatment group is significantly inhibited, and the ability of CNTN4 to inhibit the T cell activity is stronger than that of PD-L1 known as a conventional immune checkpoint protein.

The result suggests that if the function of the CNTN4 protein is suppressed, its immune escape mechanism is blocked and thus the CNTN4 recombinant proteins may be used as a disease therapeutic agent.

Example 2: Production of Monoclonal Antibodies to CNTN4

The light chain and heavy chain regions of FIG. 2 and Table 1 were cloned in an expression vector. The DNA was transient transfected into Expi293F™ cells and cultured up to 50% of viability or up to day 6 to perform IgG expression, and the culture medium was bound to protein A affinity columns (MabSelect SuRe LX, Cytiva) to elute and primarily purify IgG. Then, in order to remove aggregate and impurities having a large molecular weight, the primarily purified IgG was bound to cation ion exchange columns (Capto SP ImpRes, Cytiva) and elute and secondarily purify IgG using a concentration gradient of acetic acid buffer solution (pH 5.0) and sodium chloride. Through this, anti-CNTN4 IgG4-S228P (hereinafter, referred to as "hAb-1") having a purity of 95.9% on SEC-HPLC was prepared.

TABLE 1

| SEQ ID NO | Region | Sequence |
|---|---|---|
| SEQ ID NO: 1 | hAb-1 light chain variable region (VL) | ELTQDPAVSVALGQTVRITCSGSSGSYGWYQQKP GQAPVLVIYDNTNRPSGIPDRFSGSSSGNTASLTITG AQAEDEADYYCGGYDGSTDVFGGGTKLTVL |
| SEQ ID NO: 2 | hAb-1 heavy chain variable region (VH) | EVQLLESGGGLVQPGGSLRLSCAASGFTFSSFNMF WVRQAPGKGLEWVAEISGGGGSTWYAPAVKGRFT ISRDNSKNTLYLQMNSLRAEDTAVYYCAKSADTW SYGAATIDAWGQGTLVTVSS |

Example 3: Confirmation of Binding Ability of Monoclonal Antibody hAb-1

3.1 Confirmation of Binding Ability of Monoclonal Antibody hAb-1 to Antigenic Protein according to ELISA ELISA test was performed on the monoclonal antibody hAb-1 prepared in Example 2. An ELISA plate was coated with 20 nM of antigens (human CNTN4-10×His or mouse CNTN4-10×His). For antibody binding, antibodies hAb-1 were serially diluted from a maximum of 1 μM to 0.0001 nM, thereby binding to the antigen. HRP conjugated anti-human kappa antibodies were used as a secondary antibody for antibody detection. Color was developed using ABTS, which is a color developing reagent, and the absorbance at 405 nm was measured. The resultant binding abilities are shown in FIG. 3 and Table 2.

TABLE 2

| $EC_{50}$, nM | Human CNTN4 | Mouse CNTN4 |
|---|---|---|
| hAb-1 | 0.17 | 0.12 |

3.2 Confirmation of Binding Ability of hAb-1 to Antigenic Protein according to Surface Plasmon Resonance (SPR)

SPR test was performed on the monoclonal antibody hAb-1 prepared in Example 2. More specifically, in order to bind anti-human IgG Fc (capture antibody) using amine coupling, CM5 chip was mounted, running buffer was allowed to flow, the chip was activated, and then capture antibody was attached thereto. Dextrin to which capture antibody was not attached was deactivated using ethanolamine, and then regeneration was performed using 3M magnesium chloride to clear analytes except capture antibody. The hAb-1 prepared at a concentration of 0.05 μg/mL was allowed to flow for 30 seconds at a rate of 10 μL/min for binding. Thereafter, human CNTN4 (400 nM to 0.78 nM) prepared by sequential dilution as an antigen was allowed to flow at a rate of 30 μL/min for 3 minutes to be bound, and dissociation was performed for 5 minutes.

Then, in order to clear all analytes attached to the capture antibody, a regeneration solution (3M magnesium chloride) was allowed to flow at a rate of 20 L/min for 30 seconds, and regeneration was performed. For each concentration of antigen, binding of hAb-1, binding of antigen, dissociation, and regeneration were repeated in order. The results are shown in Table 3.

TABLE 3

| Antigen | Dissociation constant Kd |
|---|---|
| Human CNTN-4 protein | $3.56 \times 10^{-8}$M |

From this, it was confirmed that the antibody of the present invention binds to the human CNTN4 protein with high affinity.

Example 4: Confirmation Whether Monoclonal Antibody hAb-1 Competitively Binds with CNTN4 Receptor for CNTN4

An ELISA plate was coated with 20 nM of antigens human CNTN4-10×His. For antibody binding, a mixture of antibodies hAb-1 diluted to a final concentration of 0 to 1,000 nM and human CNTN4 receptors (Amyloid precursor protein, APP) diluted to 0 or 500 nM was bound to the antigens. HRP conjugated anti-human kappa antibodies were used as a secondary antibody for antibody detection. Color was developed using ABTS, which is a color developing reagent, and the absorbance at 405 nm was measured.

The results are shown in FIG. 4 and Table 4. Even when the antibodies of the present invention are incubated with the CNTN-4 receptors, the degree of binding to the CNTN-4 protein was hardly changed.

This shows that the antibodies of the present invention competitively bind to the CNTN-4 proteins in the presence of CNTN-4 receptors and has excellent binding ability.

TABLE 4

| CNTN-4 receptor concentration (Co-incubation) | $EC_{50}$, nM |
|---|---|
| 0 nM | 0.17 |
| 500 nM | 0.24 |

Accordingly, the antibodies of the present invention specifically bind to the CNTN-4 proteins even when the CNTN-4 receptors are present in the body and thus can effectively inhibit the immunosuppressive ability of the CNTN-4 proteins.

Example 5: Test about CNTN4 Neutralization Ability of hAb-1 Antibodies Using Human T Cells Similar to the experiment about CNTN4's ability to inhibit the T cell activity in Example 1, α-CD3 antibodies at a concentration of 4 μg/mL and CNTN4 recombinant proteins at concentration of 150 nM were prepared into a final 50 μL and put into a 96-well plate, and incubated at 37° C. for about 16 hours. Then, the incubated plate was washed twice with 200 μL of PBS, and 0.375, 0.75, 1.5, 3, and 6 μM of hAb-1 antibodies were each prepared into a final 50 μL in a CNTN4-treated well and put into a 96-well plate. Incubation was performed at 37 ° C. for about 4 hours. The subsequent process was carried out similarly to the experiment about CNTN4's ability to inhibit the T cell activity in Example 1.

As shown in FIG. 5, it was confirmed that the CNTN4 recombinant protein inhibited the proliferation of $CD4^+$ T cells and $CD8^+$ T cells. It was observed that the proliferation of T cells that had been inhibited by CNTN4 increased in a concentration-dependent manner of the treated hAb-1. This shows that the antibodies hAb-1 of the present invention exhibit significantly excellent ability to neutralize CNTN4.

From this, it was confirmed that the CNTN4 antibodies of the present invention effectively neutralized CNTN4 and inhibited the T cell inhibitory function thereof.

Example 6: Confirmation of Antitumor Efficacy in CT26 Syngeneic Mouse Model of Colorectal Cancer (In Vivo)

In this example, it was intended to confirm the antitumor efficacy of the anti-CNTN4 antibody of the present invention in a tumor-bearing mouse, specifically, a CT26 syngeneic mouse model of colorectal cancer.

The right flank of BALB/c mice were inoculated with $1\times10^6$ CT26 cells. After transplanting cells, the mice having a tumor size of 75 $mm^3 \leq$ tumor volume $\leq 150$ $mm^3$ were selected and randomly divided into four groups of eight mice per group (Day 0), and 10, 20, and 40 mg/kg of antibodies hAb-1 and 20.4 mg/kg of hIgG4 as a control were each administered intraperitoneally (i.p.) to the groups on day 0, day 3, day 6, and day 9. The size of the tumor was measured twice a week after the start of administration, and the difference in size from the control was expressed as TGI (%) based on the tumor size on day 12. The statistical analysis of data was performed using Graphpad PRISM 8.0, and statistical processing was performed using Two-way ANOVA and analysis was performed by a statistical two-tailed Student's t-test (*P<0.05, P<0.01, *P<0.001, ****P<0.0001 versus group 1 (hIgG4)).

The average value of the data values of eight mice in each experimental group was calculated, and the results are shown in Table 5 and FIG. 6. The administration of 10 mg/kg of antibodies hAb-1 showed an excellent tumor reduction effect. As the dose increased to 20 mg/kg and 40 mg/kg, the tumor reduction effect also increased.

TABLE 5

| | | Dose level | | Tumor volume ($mm^3$) | TGI (%)[1] |
|---|---|---|---|---|---|
| Group | Treatment | mg/kg | nmol/kg | Day 12 (n = 8) | Day 12 |
| 1 | hIgG4 | 20.4 | 140.4 | 573.75 ± 69.15 | — |
| 2 | Antibody | 10 | 70.2 | 434.52 ± 80.57**** | 24.3 |
| 3 | hAb-1 | 20 | 140.4 | 298.77 ± 95.60**** | 47.9 |
| 4 | | 40 | 280.8 | 243.83 ± 87.88**** | 57.5 |

[1](1 − (mean volume of treated tumors)/(mean volume of control tumors)) × 100%
****P < 0.0001 versus group 1 (hIgG4)

From this, it was confirmed that the anti-CNTN4 antibody of the present invention exhibits an effect of inhibiting the growth of tumor cells of colorectal cancer.

Example 7: Confirmation of Efficacy of T Cell Activity Increase in CT26 Syngeneic Mouse Model of Colorectal Cancer (In Vivo)

In this example, it was intended to confirm the effect of the anti-CNTN4 antibody of the present invention on T cell level in a tumor-bearing mouse, specifically, a CT26 syngeneic mouse model of colorectal cancer.

Mice inoculated with CT26 colorectal cancer cells according to the method described in Example 6 were divided into four groups of five mice per group, and 10, 20, and 40 mg/kg of antibodies hAb-1, and 20.4 mg/kg of hIgG4 as a control were each intraperitoneally administrated to the groups on day 0, day 3, and day 6 (a total of 3 administrations every 3 days; Q3DX3). The spleen was harvested on day 7 to obtain spleen cells. Cells, from which red blood cells were removed after spleen was ground and centrifuged, were used. In order to detect an index related to an immune factor in cells, the isolated cells were divided into two groups, and one group was treated with an immune cell activating material, thereby enabling to detect the index material. The isolated cells were incubated with antibodies, anti-CD3-PerCP/Cy5.5, anti-CD4-PE/Cy7, anti-CD45-APC/Cy7, and anti-IFNγ-FITC for CD3+, CD4+, CD45+, and IFNγ, respectively, the cells were washed with buffer, and fluorescence intensity was measured. In the case of CD3, CD4, and CD45, surface staining was performed for a marker expressed on the cell surface, and in the case of IFNγ, staining was performed using an intracellular staining method for a marker expressed in the cell. When staining, the isotype of each fluorescent substance was used to prevent misinterpretation. After staining was completed, cells were washed with a buffer to remove the remaining fluorescent substances, and then the expression of intracellular and extracellular markers was analyzed with a flow cytometer (FACS CantoII). The statistical analysis of data was confirmed through the Graphpad PRISM 8.0 program, and statistical processing was performed using One-way ANOVA, and statistical significance was verified through Dunnett's multiple comparisons test. (*P<0.05, P<0.01, *P<0.001, ****P<0.0001).

The results are shown in FIGS. 7 to 10.

FIGS. 7 to 9 show the percentage of CD4+ T cells to CD45+ cells found in the spleen (i.e., CD3+CD4+/CD45+), the percentage of CD8+ T cells to CD45+ cells (i.e., CD3+CD8+/CD45+), and the percentage of cells that secrete IFNγ among CD8+ T cells (i.e., IFNγ/CD8+), respectively. From this, it was confirmed that when the antibodies hAb-1 were used, the levels of CD4+ T cells and CD8+ T cells were almost equal or increased compared to the control (hIgG4), and in particular, the secretion of cytokine by CD8+ T cells was significantly increased compared to the control.

FIG. 10 shows the degree of reduction of tumor volume used in the analysis, and in all cases using antibodies hAb-1, the tumor volume was reduced compared to the control.

From this, it was confirmed that the anti-CNTN4 antibody of the present invention exhibits an effect of inhibiting the growth of tumor cells by increasing T cell activity, particularly, CD8+ T cell activity, and increasing cytokine secretion.

Example 8: Confirmation of Antitumor Efficacy in EMT6 Syngeneic Mouse Model of Mammary Cancer (In Vivo)

In this example, it was intended to confirm the antitumor efficacy of the anti-CNTN4 antibody of the present invention in a tumor-bearing mouse, specifically, an EMT6 syngeneic mouse model of mammary cancer, known as an immunologically cold tumor.

The experiment was performed in the same manner as in Example 6, except that the right flank of BALB/c mice was inoculated with $1\times10^6$ EMT6 mammary cancer cells.

The average value of the data values of eight mice in each experimental group was calculated, and the results are shown in Table 6 and FIG. 11. The administration of 10 mg/kg of antibodies hAb-1 showed an excellent tumor reduction effect, and as the dose increased to 20 mg/kg and 40 mg/kg, the tumor reduction effect also increased.

TABLE 6

| | | Dose level | | | |
|---|---|---|---|---|---|
| Group | Treatment | mg/kg | nmol/kg | Tumor volume ($mm^3$) Day 12 (n = 8) | TGI (%)[1] Day 12 |
| 1 | hIgG4 | 20.4 | 140.4 | 870.50 ± 101.33 | — |
| 2 | Antibody | 10 | 70.2 | 557.18 ± 175.70**** | 31.2 |
| 3 | hAb-1 | 20 | 140.4 | 483.53 ± 126.90**** | 36.0 |
| 4 | | 40 | 280.8 | 662.54 ± 243.19**** | 44.5 |

[1](1 − (mean volume of treated tumors)/(mean volume of control tumors)) × 100%
****P < 0.0001 versus group 1 (hIgG4)

From this, it was confirmed that the anti-CNTN4 antibody of the present invention exhibits an effect of inhibiting the growth of tumor cells of mammary cancer.

Example 9: Confirmation of Efficacy of T Cell Activity Increase in EMT6 Syngeneic Mouse Model of Mammary Cancer (In Vivo)

In this example, it was intended to confirm the effect of the anti-CNTN4 antibody of the present invention on T cell level in a tumor-bearing mouse, specifically, an EMT6 syngeneic mouse model of mammary cancer.

The experiment was performed in the same manner as in Example 7, except that mice were inoculated with $1\times10^6$ EMT6 mammary cancer cells and four mice per experimental group were used. For the markers CD4+, CD8+, and IFNγ+ used for detection, antibodies anti-CD4-APC/Cy7, anti-CD8-PerCP/Cy5.5, and anti-IFNγ-FITC were used, respectively.

The results are shown in FIGS. 12 and 13.

FIGS. 12 and 13 show the percentage of cells that secrete IFNγ among CD4+ T cells and CD8+ T cells found in the spleen (i.e., IFNγ/CD4+ and IFNγ/CD8+), respectively. From this, it was confirmed that when the antibodies hAb-1 were used, the secretion of cytokine by CD4+ T cells and CD8+ T cells was significantly increased compared to the control (hIgG4).

From this, it was confirmed that the anti-CNTN4 antibody of the present invention exhibits an effect of inhibiting the growth of tumor cells by increasing T cell activity, and increasing cytokine secretion.

Example 10: Confirmation of Efficacy of T Cell Activity Increase in LLC-1 Syngeneic Mouse Model of Lung Cancer (In Vivo)

In this example, it was intended to confirm the effect of the anti-CNTN4 antibody of the present invention on T cell level in a tumor-bearing mouse, specifically, an LLC-1 syngeneic mouse model of lung cancer.

The experiment was performed in the same manner as in Example 7, except that mice were inoculated with $1\times10^6$ LLC-1 lung cancer cells and three to four mice per experimental group were used.

For CD3+ and IFNγ+, which were used as a detectable marker, antibodies anti-CD3-PerCP/Cy5 and anti-IFNγ-FITC were used, respectively.

The results are shown in FIGS. 14 and 15.

FIG. 14 shows the percentage of cells that secrete IFNγ among T cells distributed in the spleen (i.e., IFNγ/CD3+). From this, it was confirmed that when the antibodies hAb-1 were used, the secretion of cytokine by T cells was significantly increased compared to the control (hIgG4).

FIG. 15 shows the degree of reduction of tumor volume used in the analysis, and in all cases using antibodies hAb-1, the tumor volume was reduced compared to the control.

From this, it was confirmed that the anti-CNTN4 antibody of the present invention exhibits an effect of inhibiting the growth of tumor cells by increasing T cell activity, particularly, CD8+ T cell activity, and increasing cytokine secretion.

The invention claimed is:

1. An anti-CNTN4 antibody or an antigen-binding fragment thereof comprising:

a light chain variable region comprising the amino acid sequence of SEQ ID NO: 1; and a heavy chain variable region comprising the amino acid sequence of SEQ ID NO: 2.

2. The anti-CNTN4 antibody or antigen-binding fragment thereof of claim 1, wherein the antibody or antigen-binding fragment thereof binds to a human CNTN4 protein with a dissociation constant (Kd) of $1\times10^{-7}$ M or less.

3. The anti-CNTN4 antibody or antigen-binding fragment thereof of claim 1, wherein the antibody or antigen-binding fragment thereof increases T cell activity.

4. The anti-CNTN4 antibody or antigen-binding fragment thereof of claim 3, wherein the T cell is CD4+ T cell or CD8+ T cell.

5. The anti-CNTN4 antibody or antigen-binding fragment thereof of claim 1, wherein the antibody or antigen-binding fragment thereof increases secretion of a cytokine.

6. The anti-CNTN4 antibody or antigen-binding fragment thereof of claim 5, wherein the cytokine is IL-2, TNFα, IFNγ, or a combination thereof.

7. The anti-CNTN4 antibody or antigen-binding fragment thereof of claim 1, wherein the antigen-binding fragment is selected from the group consisting of Fab, Fab', Fab'-SH, Fv, a single chain antibody scFv, a (Fab')2 fragment, a single domain antibody, a diabody (dAb), and a linear antibody.

8. The anti-CNTN4 antibody or antigen-binding fragment thereof of claim 1, wherein the antibody is conjugated with a drug.

9. The anti-CNTN4 antibody or antigen-binding fragment thereof of claim 1, wherein the antibody is IgG1, IgG2, IgG3, or IgG4.

10. A nucleic acid molecule encoding the antibody or antigen-binding fragment thereof of claim 1.

11. A recombinant expression vector comprising the nucleic acid molecule of claim 10.

12. A method for treating cancer, comprising administering to a subject in need thereof an effective amount of the anti-CNTN4 antibody or antigen-binding thereof of claim 1 as an active ingredient, wherein the cancer is a cancer that expresses CNTN4.

13. The method of claim 12, wherein the method further comprises administering an additional anticancer agent, or providing an additional anticancer therapy.

14. The method of claim 13, wherein the additional anticancer agent is an immune checkpoint inhibitor or a chemotherapeutic agent.

15. The method of claim 14, wherein the immune checkpoint inhibitor is one or more selected from the group consisting of an anti-CTLA-4 antibody, an anti-PD-1 antibody, and an anti-PD-L1 antibody.

16. The method of claim 13, wherein the anti-CNTN4 antibody or antigen-binding fragment thereof, and the additional anticancer agent are simultaneously administered as a single formulation, or are simultaneously or sequentially administered as separate formulations.

17. The method of claim 13, wherein the additional anticancer therapy is one or more selected from the group consisting of an immune checkpoint inhibitor, a chemotherapeutic agent, and a radiotherapy.

18. A composition for diagnosing cancer, the composition comprising the anti-CNTN4 antibody or antigen-binding thereof of claim 1.

19. A method for detecting CNTN4 proteins in a sample by using the anti-CNTN4 antibody or antigen-binding thereof of claim 1 as an active ingredient.

* * * * *

```
                        SEQUENCE LISTING


<160> NUMBER OF SEQ ID NOS: 2

<210> SEQ ID NO 1
<211> LENGTH: 101
<212> TYPE: PRT
<213> ORGANISM: Artificial Sequence
<220> FEATURE:
<223> OTHER INFORMATION: hAb-1 light chain variable region (VL)

<400> SEQUENCE: 1

Glu Leu Thr Gln Asp Pro Ala Val Ser Val Ala Leu Gly Gln Thr Val
1               5                   10                  15

Arg Ile Thr Cys Ser Gly Ser Ser Gly Ser Tyr Gly Trp Tyr Gln Gln
            20                  25                  30

Lys Pro Gly Gln Ala Pro Val Leu Val Ile Tyr Asp Asn Thr Asn Arg
        35                  40                  45

Pro Ser Gly Ile Pro Asp Arg Phe Ser Gly Ser Ser Ser Gly Asn Thr
    50                  55                  60

Ala Ser Leu Thr Ile Thr Gly Ala Gln Ala Glu Asp Glu Ala Asp Tyr
65                  70                  75                  80

Tyr Cys Gly Gly Tyr Asp Gly Ser Thr Asp Val Phe Gly Gly Gly Thr
                85                  90                  95

Lys Leu Thr Val Leu
            100


<210> SEQ ID NO 2
<211> LENGTH: 123
<212> TYPE: PRT
<213> ORGANISM: Artificial Sequence
<220> FEATURE:
<223> OTHER INFORMATION: hAb-1 heavy chain variable region (VH)

<400> SEQUENCE: 2

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Glu Ile Ser Gly Gly Gly Gly Ser Thr Trp Tyr Ala Pro Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Asp Thr Trp Ser Tyr Gly Ala Ala Thr Ile Asp Ala
            100                 105                 110

Trp Gly Gln Gly Thr Leu Val Thr Val Ser Ser
        115                 120
```